United States Patent

Macvaugh

[11] 3,998,209
[45] Dec. 21, 1976

[54] SNORING DECONDITIONING SYSTEM AND METHOD

[76] Inventor: Gilbert S. Macvaugh, 4402 Stanford St., Chevy Chase, Md. 20015

[22] Filed: Dec. 16, 1975

[21] Appl. No.: 641,226

[52] U.S. Cl. .......................... 128/1 R; 128/419 R; 317/262 S; 340/279
[51] Int. Cl.² ........................................ A61B 19/00
[58] Field of Search ............. 128/1 R, 136, 419 R, 128/422 S, 423 S; 131/170 A; 272/27 N, 27 R; 273/84, 279; 340/407; 317/262 S

[56] References Cited
UNITED STATES PATENTS

| | | | |
|---|---|---|---|
| 3,032,029 | 5/1962 | Cunningham | 128/1 R |
| 3,089,130 | 5/1963 | Wilson | 340/279 |
| 3,480,010 | 11/1969 | Crossley | 128/419 R |
| 3,696,377 | 10/1972 | Wall | 340/279 |
| 3,886,953 | 6/1975 | Pope | 131/170 A |

*Primary Examiner*—William E. Kamm

[57] ABSTRACT

Principle: Two long-standing, professionally accepted, experimental psychological teaching-learning procedures are applied in this invention, wherein Pavlovian (respondent) conditioning overlaps with Skinnerian (operant) conditioning. The snore deconditioning system described herein provides for the following phases: (1) there are applied to a snoring sleeper four mild and harmless negative reinforcers (visual, auditory, tactile, pain), each selectively, which are incompatible with the socially annoying snore behavior, in order to elicit the awakening response; (2) the person is required, after awakening, to change his head, arm and hand position and (3) the person is required to depress and to hold depressed for 15 seconds a switch in order to terminate the four negative reinforcers and which switch also simultaneously applies two positive reinforcers (gustatory and auditory) as rewards for exhibiting the behaviors (1), (2) and (3) above. Thereafter, the set is deactivated automatically until the next snore response is emitted during a subsequent sleep. The snore deconditioning system comprises means automatically responsive to a significant level of snoring by a sleeper to initiate the first phase. The step of consciously and deliberately deactivating the aversive reinforcement and activating the positive reinforcement automatically is critical to success in the procedure for conditioning the subject to sleep without snoring. There is a choice of the type of aversive stimulation, so that it can be changed if the snorer becomes habituated to one kind of aversive stimulation.

12 Claims, 9 Drawing Figures

SNORING DECONDITIONING SYSTEM AND METHOD

RELATED DOCUMENTS

The benefit of the following Disclosure Document, filed in accordance with the notices of Mar. 26, 1969 (862 O.G. 1) and Aug. 11, 1970 (879 O.G. 1), is claimed:
Title: Snore Detector and Deconditioner
Filed: June 1, 1975
By: Gilbert S. Macvaugh

BACKGROUND OF INVENTION

Snoring is a widespread problem often having serious social impact.

Snoring occurs during any stage of sleep, of which, upon awakening, there is usually no recall. Sometimes a snorer is abruptly awakened, perhaps by his own snoring, but has only a vague recollection of the instant of awakening. His awareness of his own snoring is very brief and only momentary. In most instances, he soon forgets that he was aroused by his own snoring noise and starkly will deny that he was snoring. Therefore, because of the lack of awareness of snoring, a snorer may realize, in an intellectual way, that he does snore, but usually does not believe, in a passionate personal way, the magnitude of the impact of his snoring on others. Because of the lack of awareness while sleeping, the subject is unable to control that physically audible behavior by the exercise of his own decision. As a result, many procedures and devices have been tried to assist a snorer in overcoming his problem.

For example, (1) uncomfortable objects, such as balls, have been sewn into the back of a sleeping garment, in an effort to prevent the snorer from sleeping on his back. This is seldom efficacious, because the snorer continues to snore in the now uncomfortable position, or, if he changes position, continues to snore in a new posture. It is to be noted that snoring can take place in any sleeping posture.

As another example, (2) sleep learning techniques, in which a recorded message is played back to the snorer while he sleeps, the message counseling him to try to stop snoring and how to do so, have been attempted. These attempts have not been successful, any more so than the attempts to instill academic knowledge by sleep learning.

The system of the invention is based on the following principles:

A. Snoring is to be detected by a sound sensing device or by a human attendant promptly when it commences and is to be treated immediately.

B. The snorer, upon detection of snoring, is to be promptly awakened by aversive reinforcement, said aversive reinforcement being mildly unpleasant, initially.

C. When awakened the snorer must purposefully respond by switching off the aversive reinforcement.

D. The snorer then recieves two brief pleasant stimulations.

E. The snorer must continue to hold the aversive stimuli off for a predetermined period of time.

F. The snorer then relaxes and returns to sleep.

G. There are several aversive reinforcement of different kinds available, and these are used at different times, either in combination or separately. Thus, the snorer does not become habituated to any one aversive reinforcement and continues to be easily awakened when he commences to snore. Furthermore, an automatic sequence of different, progressively more unpleasant, stimuli is available.

DETAILED DESCRIPTION

Figure 1:
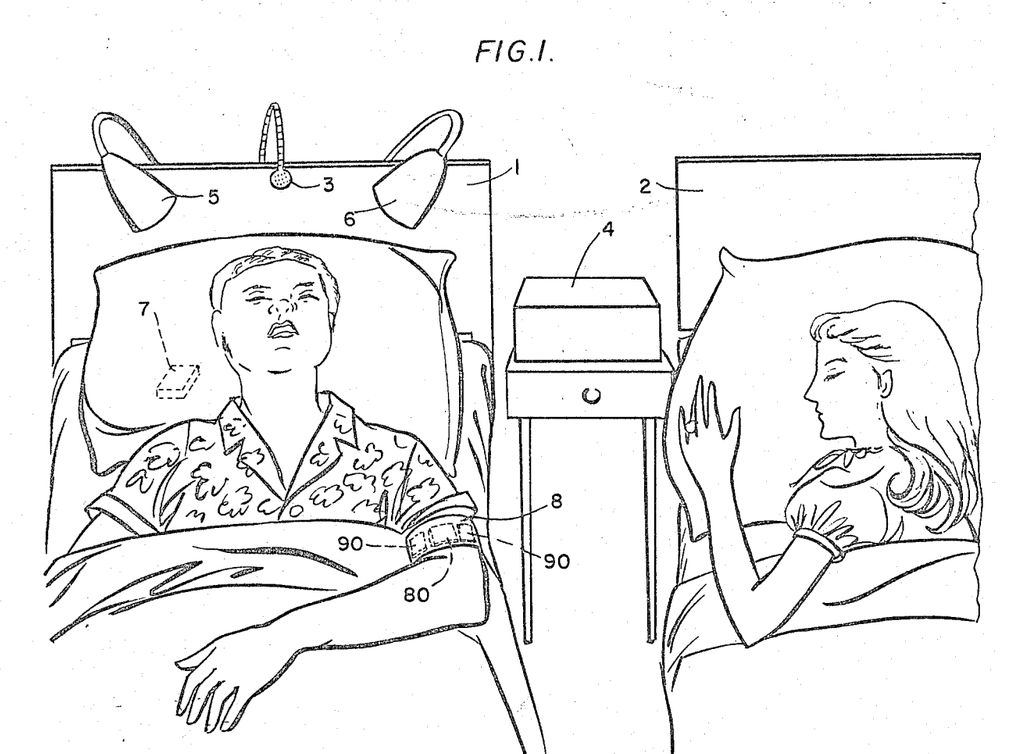
FIG. 1 is a perspective view of one embodiment of the invention in use.

Referring to FIG. 1, there is seen a pair of beds 1 and 2 for husband and wife. It is assumed, for the sake of exposition, that the husband has a snoring problem. Accordingly, his bed 1 is provided with a microphone 3 which picks up the sound of the snoring. The microphone is connected to control console 4 which contains electric circuits to be described below.

While the husband has been depicted as sleeping on his back, and about to snore, it is to be noted that objectionable levels of snoring can occur in any sleeping position of the body. Therefore, the system of the invention is dependent, not on the position of the snorer's body, but only on the level of sound produced during snoring.

When the snoring exceeds a chooseable predetermined auditory level for a chooseable predetermined time, the control console 4 activates various aversive stimuli sources, either singly or in combination, or in a predetermined sequence, depending on the way the operator has set the controls. It is to be noted that the controls can be set in accordance with instructions provided with the device or from a coach, such as a consulting psychologist, or in accordance with the desires of the wife, or in accordance with the patient's own judgement.

When the electric circuits in the console 4 determine that snoring of more than the predetermined magnitude has occurred for the predetermined time, the said circuits activate aversive stimuli sources, in a manner to be described below. These aversive stimuli sources are (1) electric lamps 5 and 6, which project an intense light on the sleeper's head area, which intense beam may be either steady or flickering; (2) a pillow buzzer 7, which produces a sound readily heard by the sleeper, whose head is in contact with the pillow; and a cuff device 8. The cuff device 8 includes a source of two different stimuli. The first of these two (3) is a device 80 for tapping the arm. This consists of a vibratory electro-magnet device having a clapper, and in which the clapper hits the patient's arm rather than a doorbell. The second of these two (4) is a pair of electrodes 90 which are energized by a periodic voltage of spike-like waveform to provide a mild electric shock.

Each of the sources of aversive stimuli 5, 6, 7 and 8 is connected to the console 4 by suitable electric conductors which, in order to simplify the drawing, are not shown.

Figure 2:
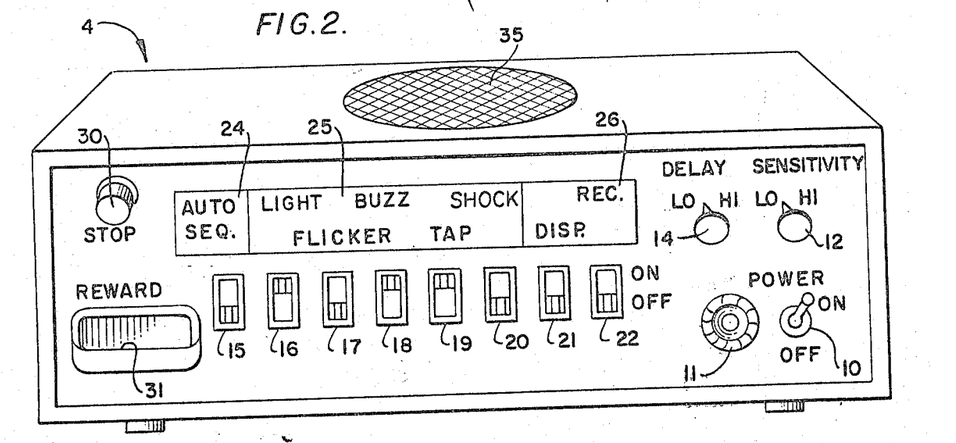
FIG. 2 is a perspective detailed view of the outside of the control console of the said embodiment.

FIG. 2 is a perspective view of the console 4. A description of the protocol for use of the equipment will make clear the operation of the circuitry to be described later.

When the equipment is in use, the power switch 10 is turned on, lighting the pilot light 11. The sensitivity knob 12 is adjusted to a desired threshold. For example only, the wife must adjust sensitivity knob 12 to a medium value, corresponding to a medium level of snoring which she does not find objectionable. Or the husband, as his training progresses, may progressively set the sensitivity knob 12 to a more sensitive setting. The delay knob 14 is adjusted to a desired setting, corresponding, say, to two seconds. This would hold the equipment inactive for two seconds after snoring commenced, and thereby prevent activation by a single snore-like sound of a half second duration. Such delays are common in many kinds of alarm systems to prevent false operation, and the effect would be similar here.

The slide switches 15 to 22 are adjustable up (on) or down (off) as desired. The function of each slide switch 15 to 22 is indicated by the legends directly above them in labels 24, 25 and 26.

Label 25 refers to various aversive stimuli of progressively more noticeable nature, going from left to rigt.

"Light" slide switch 16 controls the lights 5 and 6, to either permit them to light when snoring occurs or to keep them off.

"Flicker" slide switch 17 determines whether the lights 5 and 6, when energized, produce a steady light or whether they flicker. It is to be noted that a flickering light is far more noticeable than a steady light, especially if the flicker is fairly rapid, say, about five times a second.

"Buzz" slide switch 18 determines whether the pillow buzzer 7 is energized during snoring. Similarly, "Tap" slide switch 19 determines whether the tapping means in cuff 8 is activated at that time and "Shock" slide switch 20 determines whether the shocking electrodes in cuff 8 are energized.

The legend "Auto. Seq." on label 24 indicates, when switch 15 is activated to the up (on) position, that the aversive stimuli are applied automatically in a predetermined sequence. After the microphone 3 has picked up loud enough snoring for a sufficient time to activate the aversive stimuli, the sequence is as follows:

For the first five seconds, only the lights 5 and 6 come on, either steady or flickering, depending on the setting of "Flicker" slide switch 17.

During the second five-second period, the lights still being on, the pillow buzzer 7 is also activated.

During the third five-second period, the lights and buzzer still being on, the tapper in arm cuff 8 is also activated.

During the fourth five-second period, the light, buzzer and tapper still being on, the shocking electrodes in arm cuff 8 are activated.

The entire battery of four aversive stimuli means continues to be activated for another five seconds, at which times the entire battery of four aversive stimuli means is briefly deactivated for about a second, whereupon it is again activated. The five-second cycle of "on", followed by a brief "off" period, continues to repeat until the snorer awakens and turns off the aversive stimuli, as explained below.

It is to be noted that, in our experience, no sleeper has ever slept through the initial cycle of the four aversive stimuli, so the flashing on and off of all four aversive stimuli may never be needed, but is is available, if necessary, for an exceptional sleeper.

At the time the aversive stimuli means were first activated, a light started to glow inside "STOP" push button 30, rendering it readily findable in a darkened room or at night. When the aversive stimuli awakens the snorer, he rouses enough to find "STOP" push button 30, and hold it depressed. This immediately deactivates the aversive stimuli. Before the sleeper can resume his sleep he must hold the "STOP" button 30 down for 15 seconds, by which time he is fully awake. If he fails to hold the STOP button 30 down for 15 seconds, the aversive stimuli are reapplied at the moment of release of the STOP button 30.

The depression of push button 30 for the required period also will activate two pleasant stimuli, depending on the setting of slide switches 21 and 22.

"Disp" slide switch 21 controls the dispensing of a confection, such as a mint or an "M&M" into the chute 31. This is a form of reward for completing the required task of awakening, changing his position in bed, and pressing the lighted STOP button 30.

"Rec" slide switch 22 controls the playing back of a pre-recorded audible message through loudspeaker 35. The message may, for example, be one from the patient's coach, saying: "You have followed instructions and pressed the lighted button long enough, until the light in the button went out. Well done." Or the message might be: "You performed well, you awoke, changed your position, pressed and held the lighted button to remove the annoying stimulations, ate the candy, listened to this message, all to help you to stop snoring. Keep up the good work. Please return to sleep in a new position."

From the description thus far, it is seen that the equipment is flexible, and can be adjusted to the needs of different patients, or for the needs of different experiments. This is accomplished by the circuitry in the control console, more fully shown in FIG. 3.

Figure 3:
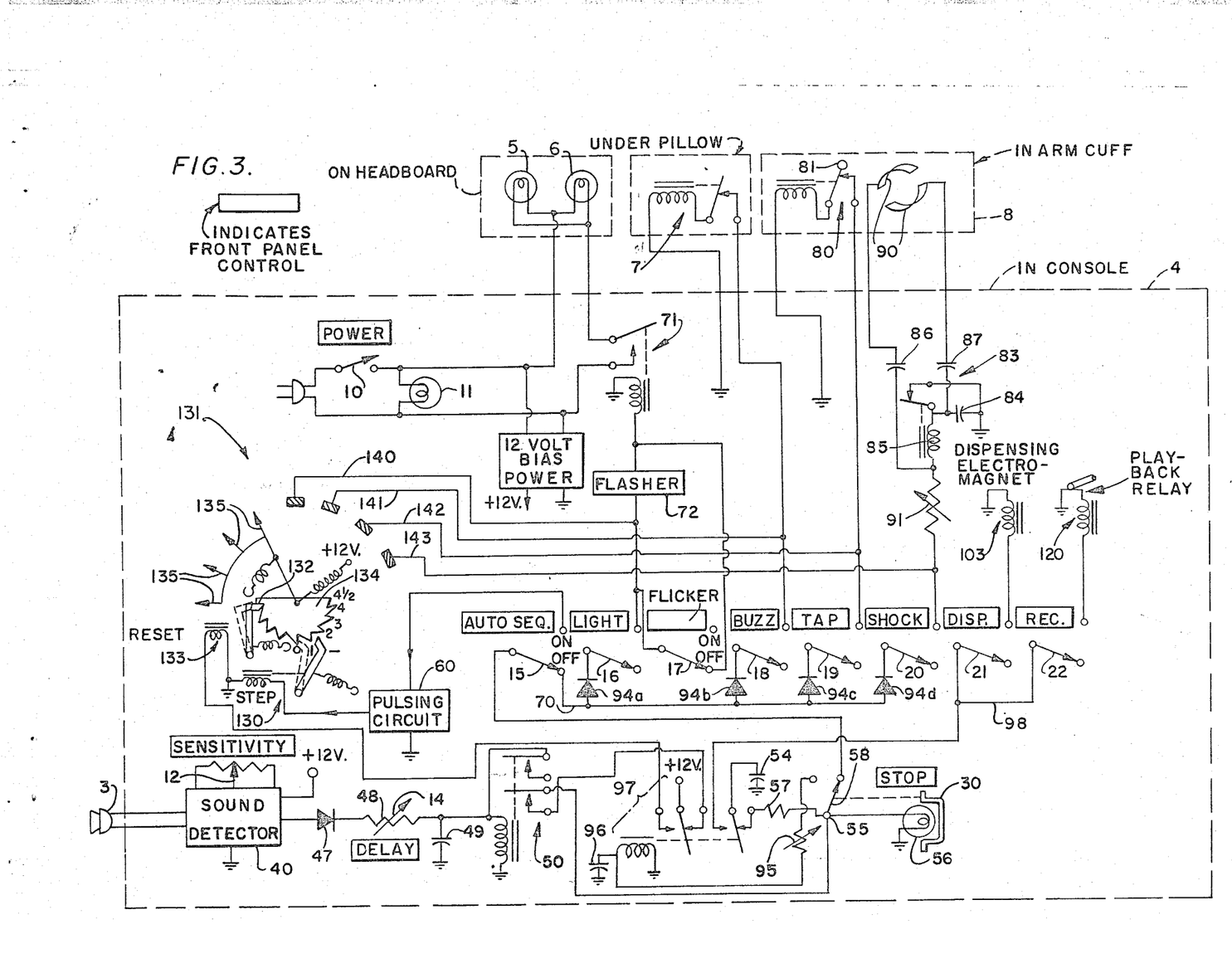
FIG. 3 is a schematic diagram of one exemplary embodiment of the electrical circuits of the said embodiment.
Figure 4:
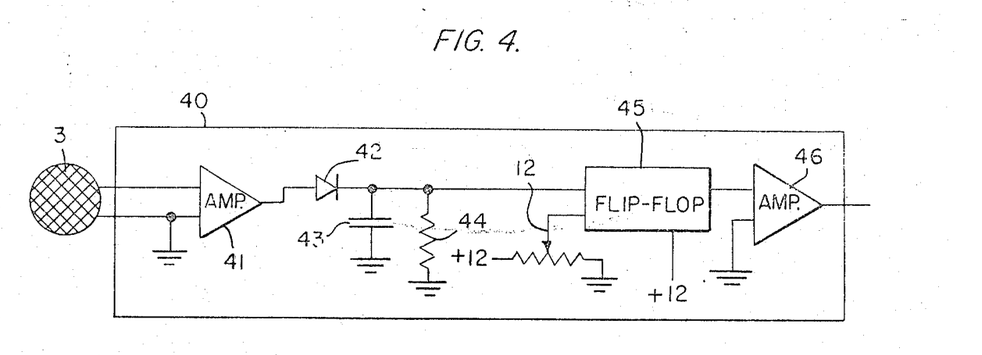
FIG. 4 is a schematic diagram of the sound detector used in the said embodiment.

The microphone 3 is connected to the sound detector 40, which is shown in greater detail in FIG. 4.

The pickup microphone 3 feeds an input amplifier 41, the output of which is rectified in diode 42 and integrated in capacitor 43. A leakage resistor 44, in conjunction with capacitor 43, provides a discharge time constant of about a second, so that the sound detector 40 can respond to a moment of silence after a sudden burst of noise. The level of the sound signal, as stored in capacitor 43, is compared with the voltage determined by the setting of sensitivity control 12. If the sound signal is greater, the output of flip-flop 45 is positive-going, otherwise the output of the flip-flop is zero. The output of the flip-flop is amplified in power amplifier 46 (an emitter-follower) and applied through a diode 47 and adjustable delay resistor 48 to storage capacitor 49. Connected in shunt to storage capacitor 49 is a relay 50. By adjusting the valve of delay resistor 48, the pull-in time of relay 50 can be varied from almost instantaneous to 10 seconds. Thus, the system is so constructed that a brief single spurt of snoring can be, at the selection of the user, either ignored or responded to.

If desired, electrical filters of either active or passive type can be inserted into the sound detector 40, so as to enable it to be more responsive to the frequencies characterizing an individual's snore sounds than to other ambient frequencies. However, since the component frequency of snore sounds has a rather broad band distribution, it is thought that the addition of such filters is not economic, and they have not been included in the circuit of FIG. 3, but in some models of this invention, they definitely will be included.

Figure 9:
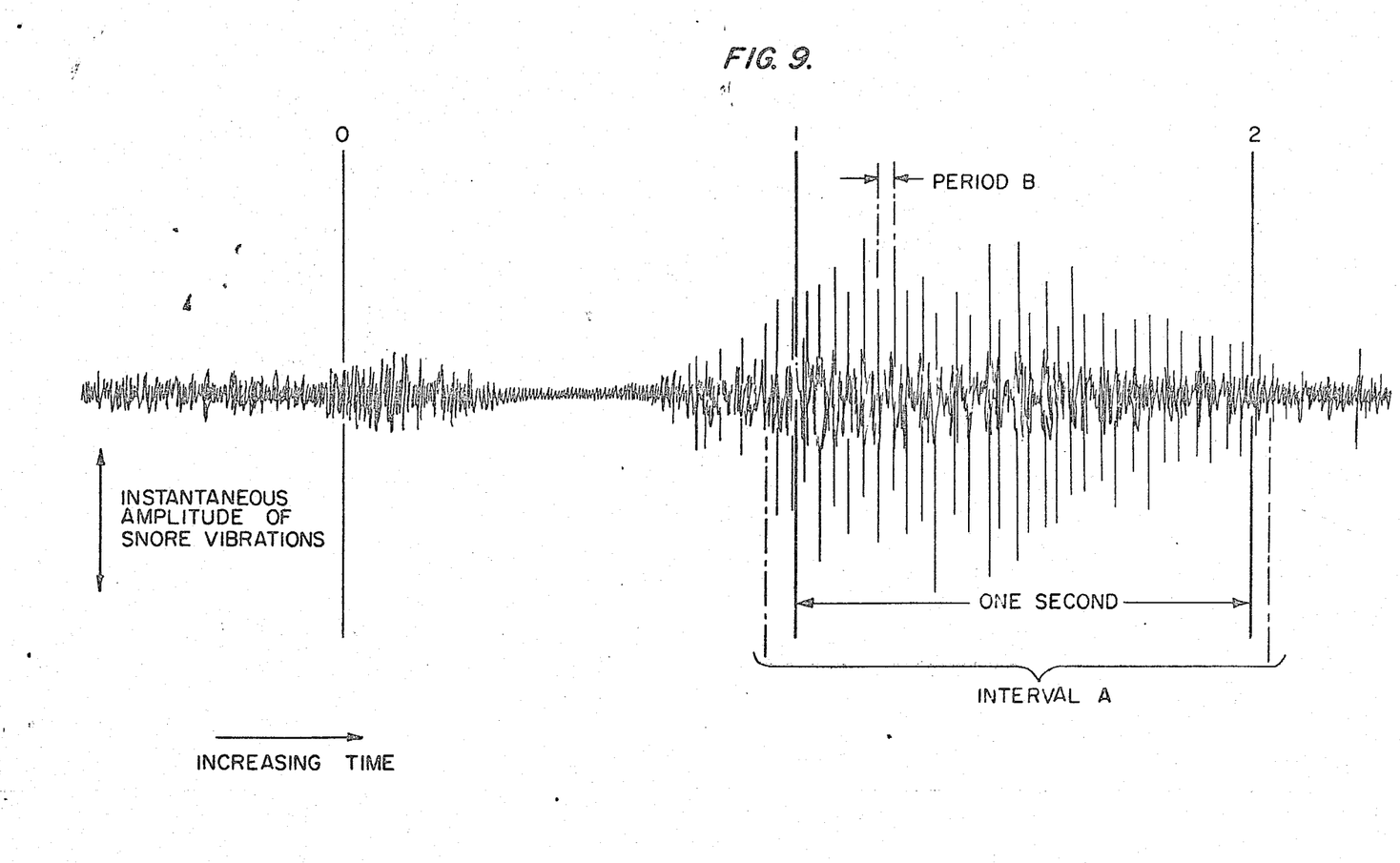
FIG. 9 is a graph showing the instantaneous amplitude of the vibrations of a typical snore sound plotted against time.

The nature of snoring sounds can be seen from the graph of FIG. 9. This graph is copied from a plot produced by a Honeywell Visicorder, to which tape recorded electrical signals of snoring sounds have been fed. The snore vibrations of the graph can be studied in various ways, such as studies to understand snore responses better. For the present purpose, it is to be noted that the graph contains a large number of sharp spikes, indicating that the frequency components of the signal occupy a broad band, similar to that of white noise. However, during interval A, at the height of a snore sound, the larger spikes occur at somewhat similar intervals, one of which is labeled Period B. The existence of spikes at somewhat similar intervals indicates that snore sounds comprise a strong component of sound frequencies concentrated in a narrow band whose center frequency is the reciprocal of the average period of the spikes. Thus, it would be feasible to use a narrow band-pass filter, centered on that frequency, in the sound detector 40, to enable the sound detector to selectively respond to those frequencies during interval A. The particular frequency depends on the anatomy of the snorer, and would be different for different snorers.

When relay 50 pulls up, it establishes a holding circuit for itself through its upper contact from the +12 volt bias source. The lower contact meanwhile energizes a junction 55 from the same bias source.

Junction 55 energizes the lamp 56 within the lighted push button 30 so that the push button glows. Junction 55 energizes a capacitor 54 through a current limiting resistor 57. Junction 55, through the single pole double throw switch 58 (controlled by push button 30) energizes the "Auto Seq" slide switch 15.

The automatic sequence slide switch 15 acts as a bias power distributor. In the On positon, it sends +12 volt bias power to the pulsing circuit 60, to be described below. In its Off position the automatic sequence slide switch 15 energizes bus bar 60.

When bus bar 70 is energized with +12 volt bias, several aversive stimuli circuits can be actuated by the closing of slide switches 16, 18, 19 or 20.

If Light slide switch 16 is closed, while bus bar 70 is energized, lamps 5 and 6 become lit by action of relay 71. The control path to relay 71 is through flasher 72, which is short circuited, and therefore ineffective, if Flicker slide switch 17 is in the Off position. If Flicker slide switch 17 is in the On position, so that it does not short circuit the flasher 72, the flow of energizing current through the flasher periodically causes the flasher 72 to open circuit, so that relay 71 drops out and lamps 5 and 6 turn off. The operation of the flasher is similar to the operation of a flasher unit in an automobile turn signal, but the period of the flash, instead of being more than a second, as it is in automobiles, is preferably much shorter, as a flicker rate of about 10 cycles per second is more noticeable.

When bus bar 70 is energized, if Buzz slide switch 18 is closed, the pillow buzzer 7 is energized and can be heard through the pillow. Similarly, if Tap slide switch 19 is closed, the tapper 80 in cuff 8 is actuated and clapper 81 tactilely stimulates the sleeper's arm.

When bus bar 70 is energized, if Shock slide switch 20 is closed, the electromechanical circuit interrupter 83 is energized. This interrupter is provided with a capacitor 84 across its break contact and with a highly inductive energizing coil 85, so that, as also in automobile ignition systems, a high voltage ringing voltage develops across the coil 85 at the moment the interrupter contacts break. This high voltage is conducted by safety isolation and current limiting capacitors 86 and 87 to electrodes 90 in arm cuff 8. The magnitude of the shock should be unpleasant but not painful, namely, about 15 milliamperes peak current during the short spikes. This magnitude is set by adjusting resistor 91, which is located within the console and which is therefore accessible only to the electronic technician.

It will be noted that slide switches 16, 18, 19 and 20 are connected to bus bar 70 by way of diodes 94a, 94b, 94c and 94d, respectively. These diodes act as conductors during the just-described operation and can be ignored. However, during the automatic sequencing operation, to be described below, these diodes act as isolating means for the different aversive stimuli means, by preventing any sneak circuits between said means through bus bar 70.

When, after responding to the aversive stimuli, the snorer awakes, he presses the lighted STOP push button 30. This throws switch 58 to its left contact, immediately removing +12 volt bias, coming from junction 55, from bus bar 70, and thereby immediately removing the aversive stimuli. However, if the patient releases STOP push button 30, before the expiration of 15 seconds, the released switch 58 reestablishes the +12 volt bias on bus bar 70. Accordingly, the patient, in order to avoid the aversive stimuli, must continue to depress the STOP push button 30 for 15 seconds, and during this time he is roused fully. During these 15 seconds, switch 58 transfers +12 volt bias to its left contact and slowly charges storage capacitor 96 through adjustable current limiting resistor 95. The storage capacitor 96 is shunted by the energizing coil of relay 97. The values of the components and the adjustment of resistor 95 is such that relay 97 pulls up after 15 seconds.

The pulling up of relay 97 has several consequences. It removes +12 volt bias supply at its left armature from the holding circuit of relay 50, so that relay 50 drops out. when relay 50 drops out, the energizing circuit for junction 55 is interrupted at the lower contact of relay 50, so that lamp 56 is extinguished and bus bar 70 is deenergized. The extinguishment of the lamp 56 within the lighted STOP push button 30 indicates to the patient that he can cease to depress the push button, without reactivating the aversive stimuli means. It will be noted that when relay 97 pulls up, the consequent interruption of +12 volt bias at junction 55 removes energizing power for relay 97, so, immediately after relay 97 pulls up, it drops out. Although relay 97 pulls up only very briefly, this brief time is sufficient to permit relay 50 to drop out, since relay 50 is quick acting and since relay 97 is retarded by use of a copper slug, as is well known in the art.

At the moment when relay 97 is pulled up, it also connected, at its right armature, the capacitor 56, (which previously had been charged to +12 volt bias from junction 55) to the bus bar 98.

Figures 5, 6, 7:
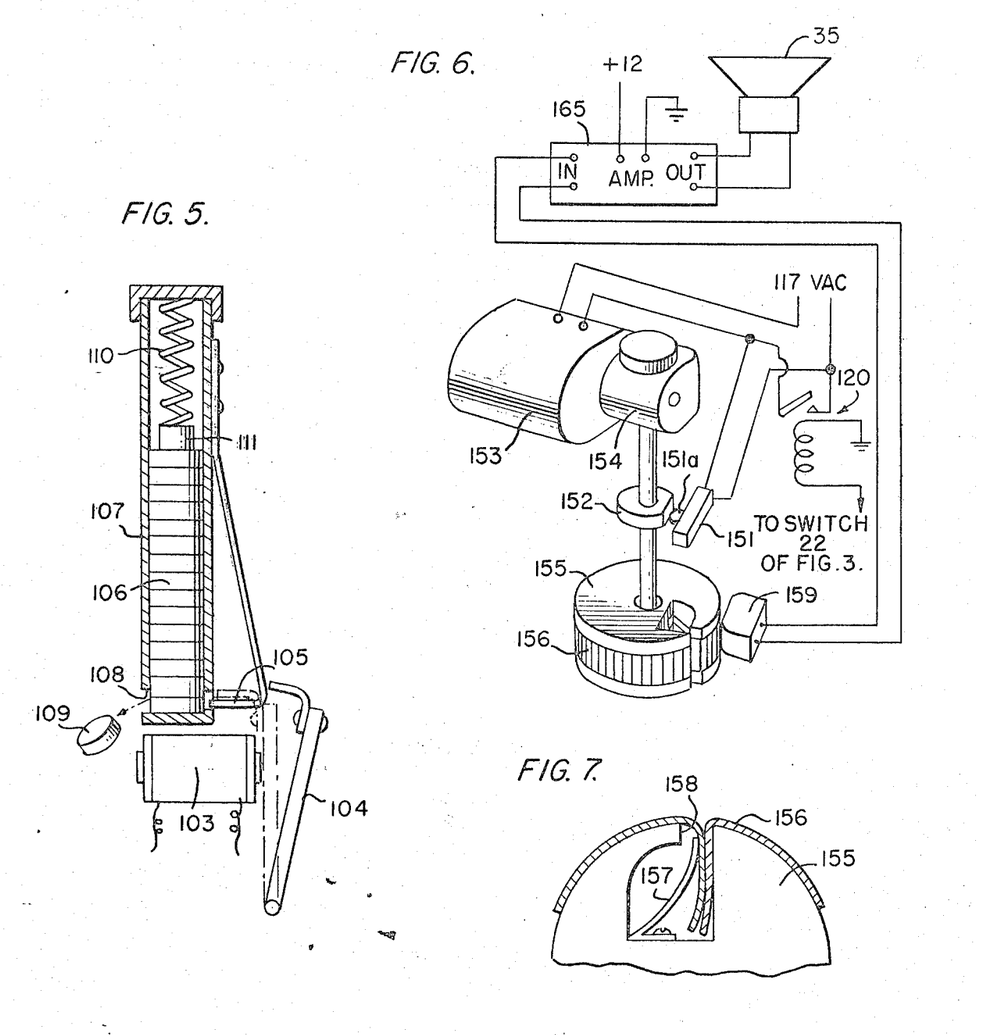
FIG. 5 is a diagram of a typical dispensing means which can be used with the invention.
FIGS. 6 and 7 are, respectively, a general view of an audible message playback system which can be used with the invention and a detail of a portion thereof.

Energized bus bar 98, when Disp slide switch 21 is closed, energizes dispensing solenoid 103. As seen in FIG. 5, dispensing solenoid 103 attracts armature 104, which moves pusher spring 105 to the left, thereby stripping one of the stack of confections 106 in magazine 107 and ejecting it out of the port 108, as shown at 109, whereupon the confection falls into the chute 31 seen in FIG. 2. The magazine 107 is provided with pusher spring means 110 which presses the follower 111 against the stack of confections 106. The patient can then take the confection out of the chute 31 and experience this positive reinforcement as he falls back to sleep in a different sleeping posture. It is to be noted (with a view to training a small child to sleep without snoring) that the patient cannot obtain multiple confections by multiple actuations of the STOP push button 30, but than only one confection is delivered upon the completion of each cycle, from snoring to awakening to actuation of push button 30.

If Rec slide switch 22 is closed when bus bar 98 is energized, playback relay 120 is energized, thereby causing the audible playback of a pre-recorded positive reinforcement message through loudspeaker 35 (FIG. 2), as further explained below.

It is to be noted that capacitor 54 holds a sufficient charge so that when relay 97 pulls up, both electromagnet 103 and relay 120 would be actuated if their respective slide switches 21 and 22 were closed.

If the Auto Seq slide switch 15 is moved from the off contact to the on contact, +12 volt bias is removed from bus bar 70 and is applied, instead, to pulsing circuit 60. Pulsing circuit 60 thereupon initially and briefly energizes stepping magnet 130 of rotary switch 131, and continues briefly to reenergize stepping magnet 130 every five seconds thereafter. The pulsing current is on for about a second and is off for the remainder of the five-second cycle time.

The stepping magnet 130, in conjunction with pawl 132 of reset latch 133 and the ratchet 134, advances rotor wiper contact 135 around one step each time the stepping magnet 130 is energized. With the initial energization, the first rotor wiper contact 135 makes contact with the stator contact on conductor 140, and with the next energization, the first two rotor wiper contacts 135 make contact with the stator contact on both conductors 140 and 141. Thus, as the sequence of stepping pulses arrives from pulsing circuit 60, the conductors 140, 141, 142 and 143 are progressively energized. As the rotor wiper contacts 135 jump to each new position, the previously energized ones of conductors 140 to 143 are momentarily deenergized because of the presence of the gaps between the rotor wiper contacts 135. When the rotor wiper contacts 135 have been stepped four times, so that the first rotor wiper contact makes contact with the stator contact for conductor 143, it cannot advance to a fifth or further position, because the next and last tooth of the ratchet 134 is in a half-height tooth which corresponds to 4½, and the pawl 132 cannot hold the ratchet at the 4½ position, but lets it slip back to a position corresponding to 4. Accordingly, from then on, every five seconds, all of the conductors 140 to 143 are briefly deenergized while the stepping switch 131 is briefly in the 4½ position, and then are reenergized when the stepping switch 131 falls back to the 4 position.

The conductors 140, 141, 142 and 143 are directly connected to the following aversive stimuli sources respectively: lights 5 and 6, pillow buzzer 7, tapper 80 and shocking electrodes 90. Thus, as the stepping switch operates, a series of progressively more aversive stimuli is applied to the snorer, and finally, all of these stimuli are simultaneously applied and periodically deenergized with a five second pulsation.

It has been found that even a heavy sleeper will awake promptly when these four adversive stimuli are applied simultaneously.

When the patient who has experienced the Auto Seq mode presses the STOP button 30, the aversive stimuli are instantly removed, as the mode previously described. Further, the reset relay 133 is actuated by the left armature of relay 97, so that the rotor wiper contacts 135 are reset to their initial or zero position by one of the three attrahently biased springs of stepping switch 131, which springs are shown in FIG. 3.

The above describes that part of the invention which is designed (1) to punish the snorer for his snoring by awakening him; (2) to make him change his position from the snoring posture in bed; and (3) to make him remove the aversive stimulations by pressing the button 30 as part of the process of deconditioning him from the snoring behavior.

The following description pertains to that part of the invention which rewards him in two ways for having responded appropriately as part of the deconditioning process.

The playback relay 120, when energized, initiates the playing back of a pre-recorded message. As seen in FIG. 6, the playback relay 120 is connected in shunt to a switch 151. Switch 151 is an off-normal switch, actuated by cam-follower 151a, and is closed during the normal rotation of cam 152 but opens when the cam follower senses the low point of the drop-off. That low point can be considered the normal point with reference to the operation described below. Switch 151 and relay 120 jointly supply energizing power to motor 153, which, through gear reduction 154, drives the cam 152 and drum 155. It will be seen that whenever relay 120 is briefly pulled up, the motor 153 begins to rotate, and thereby, by establishing an energizing circuit through off normal switch 151, continues to rotate until cam 152 and drum 155 have completed one rotation, whereupon the motor stops when switch 151 opens upon the cam reaching its normal position.

The drum 155 carries a magnetic tape 156 about its periphery. The tape 156 carries a pre-recorded message, and the message can be changed by substituting a different tape with a different message. This is done by means best seen in FIG. 7.

A length of tape 156 is wrapped about the drum 155 and its ends are stowed in notch 158, where the stowed ends are secured by spring 157.

The message tape 156 is sensed by pickup head 159 and is amplified in amplifier 165, which feeds loudspeaker 35.

The particular circuits shown in FIG. 3 are presented as illustrative. These circuits are typical of those which would be routinely designed by technicians to satisfy the requirements defined in the description above of the operation of the control console of FIG. 2. It is to be taken for granted, that in the present transistor age, solid state circuits could be used in place of the stepping switch, the various electromechanical relays and the electromechanical interrupter 83.

The above described embodiment utilizes automatic auditory sensing means and automatic sequencing means. These means can be omitted in a simplified embodiment, described below. In it the automatically performed functions of the above embodiment are, to some extent, manually performed by an attendant. The attendant may be someone in professional relationship with the snorer, such as a psychologist or nurse, or may be someone who is concerned or annoyed by the snorer's sound, such as an intimate family member.

Figure 8:
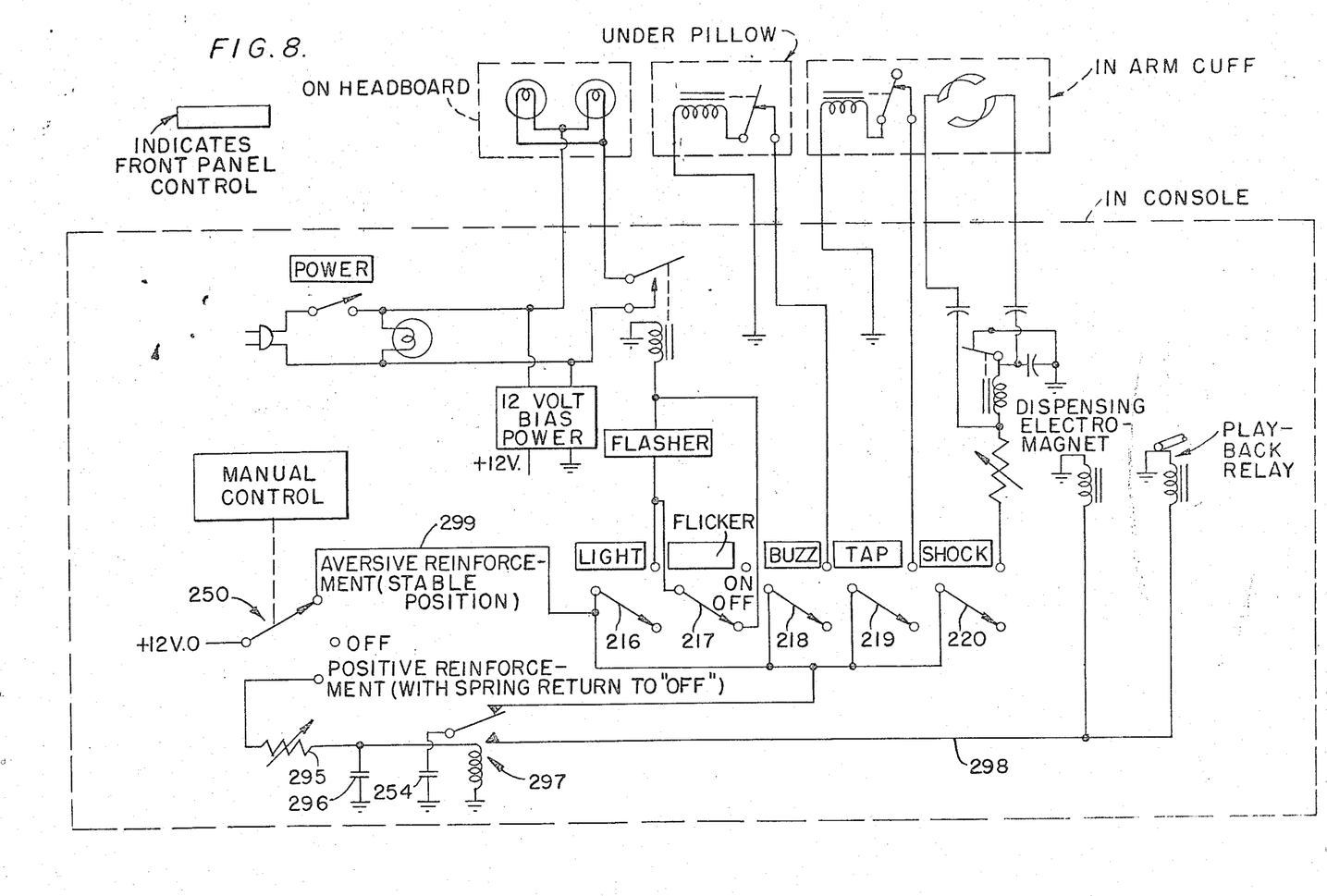
FIG. 8 is a view of the circuit of a different embodiment of the invention, in which the preferred sequencing of stimuli is initiated by an attendant.

FIG. 8 discloses the circuit diagram of this simpler embodiment. Most of the circuit is similar to that already described, as is evident by comparison with the circuit of FIG. 3, and the common subject matter need not again be described.

The simplified embodiment utilizes a single pole double throw toggle switch 250, which is of the three-position type. In the center or neutral position, the switch makes no connections between any circuits connected to the switch, and this position is labeled Off. The toggle switch also has a thrown position in which the upwardly thrown moveable wiper connects 12 volts bias power to conductor 299 by way of the upper stator contact. When the switch is thrown into this position, it remains there until manually reset. The upper thrown switch position is labeled Aversive Reinforcement. The toggle switch 250 also has an oppositely thrown position in which the downwardly thrown wiper connects 12 volt bias power to adjustable resistor 295 by way of the lower stator contact. The downwardly thrown position is labeled Positive Reinforcement.

The circuit of FIG. 8 does not utilize diodes, such as diodes 94a to 94d, because there is no problem of sneak circuits in FIG. 8, unlike the more complex circuit of FIG. 3.

The operation of this embodiment is made clear by considering the protocol for use, it being assumed, for purpose of exposition, that the actors are the snorer and a person concerned or annoyed by the snoring. The protocol follows these steps:

1. Before retiring, the concerned or annoyed person, hereinafter designated CP, connects the device to AC house current.

2. When CP hears a snore sound, CP immediately moves switch 250 to the aversive reinforcement position, thereby energizing conductor 299 from the 12 volt bias power source and enabling the application of aversive stimuli, conditional on further action, as described below.

3. CP also actuates switch 216, which turns on the lights on the headboard. CP waits about five seconds to see whether the snorer awakens.

4. If the snorer does not awaken, CP then actuates slide switch 217, which causes the headboard lights to flash. CP waits three seconds to see whether the snorer awakens.

5. If the snorer does not awaken, CP then actuates slide switch 218, which causes the pillow buzzer to sound. The headboard lights continue to flash while the pillow buzzer sounds. CP waits three seconds to see whether the snorer awakens.

6. If the snorer does not awaken, CP actuates slide switch 219, which actuates the tapper in the arm cuff. Meanwhile, the flashing lights and the pillow buzzer continue to operate. CP waits three seconds to see whether the snorer awakens.

7. If the snorer does not awaken, CP actuates slide switch 220, which actuates the shocking electrode in the arm cuff.

8. When the snorer awakens in reponse to the application of any of the aversive stimuli, as described above, he will continue to be subject to the aversive stimuli until he has changed his position and reached over to turn switch 250 to the off position, whereupon the aversive stimuli immediately cease.

9. The awakened snorer, in accordance with instructions supplied, for example, with the device or by a psychologist, will further actute switch 250 to the positive reinforcement position and hold it there till he is rewarded. When he does this, the capacitor 296 slowly charges up towards the 12 volt bias level by means of current supplied by variable resistor 295 and switch 250. After a time delay determined by the magnitude of the resistance of resistor 295 and the capacitance of capacitor 296 and the impedance and pull-in value of relay 297, the relay 297 pulls in, and transfers its moving armature from the break contact to the make contact. The break contact had previously charged capacitor 254 to the bias voltage, and when the moving armature touches the make contact the charge in capacitor 254 is transferred, by way of conductor 298, to the dispensing electromagnet and the play-back relay. The snorer is thereupon rewarded with a morsel and a recorded congratulatory message. It will be noted that repeated actuation of switch 250 to the reinforcement position will not result in multiple actuation of the dispensing solenoid, because capacitor 254 can only be charged when switch 250 is in the aversive reinforcement position, because the charge is derived from conductor 299.

10. If the snorer does not, after awakening, hold the switch 250 in the positive reinforcement position for the required period of time, but merely puts it into the off position, CP immediately throws switch 250 back to the aversive reinforcement position, thereby applying all the previously used aversive stimuli to the snorer. CP continues to do this until the snorer has awakened enough to eat the morsel and to listen to the congratulatory message. If he has done this, the switch 250 will be in the off position, because of the spring-return action from the positive reinforcement position. The snorer can resume sleeping.

11. When the snorer has completed his assigned task and is returning to sleep, CP returns the switches 216 to 220 to their off position.

It will be seen that at the end of the cycle, the snorer has recieved visual, auditory, tactile and pain stimuli as punishment for snoring and has received positive gustatory and auditory stimuli as reward for ceasing snoring. Thus, the snorer has passed through a snore deconditioning event.

I claim:
1. In combination:
means responsive to audible snoring coming from a sleeper, said means producing an output signal when said snoring has exceeded a predetermined level of loudness for a predetermined time;
means responsive to said output signal for producing aversive stimuli and applying said aversive stimuli to said sleeper, whereby said snoring sleeper is punitively roused in order to awaken to make him change position and require him to perform specific tasks as part of the deconditioning process;
manually actuatable means for terminating said aversive stimuli, for an initial period of time, only while the manually actuatable means is actuated, and for terminating said aversive stimuli during a following period of time, without regard to the actuation or non-actuation of said manually actuatable means, as soon as the manually actuatable means has been continuously actuated for a period of time equal to said initial period of time;

whereby, in order to terminate said aversive stimuli, said sleeper must continuously actuate said manually actuatable means for said initial period of time, whereby said sleeper awakens fully while actuating said manually actuatable means.

2. The invention of claim 1 in which the initial period of time is from 5 to 30 seconds.

3. The invention of claim 1 in which
the aversive stimuli means comprises plural sources of stimuli of different types, stimulating different senses of the sleeper.

4. The invention of claim 3, in combination with manually controllable means for selecting particularly ones of said aversive stimuli means for actuation and non-actuation.

5. The invention of claim 3, in combination with manually controllable means for selecting an automatic sequence of progressively more unpleasant aversive stimuli means for actuation.

6. The invention of claim 3, in which one of the aversive stimuli means is a strong light;
and manually selectable means for causing said strong light, when actuated, to either burn steadily or to flicker.

7. The invention of claim 3, in combination with means for providing pleasant stimuli;
means responsive to the actuation of said manually actuatable means to activate said means for providing pleasant stimuli as a reward for awakening, changing his position in bed and performing specific tasks as part of the snore deconditioning process.

8. The method of fully awakening a snorer which consists of the steps of:

detecting any snoring from said snorer which exceeds a predetermined level of intensity for a predetermined periof of time;

applying aversive stimuli to said snorer in response to said detection, said stimuli being sufficiently noticeable and unpleasant to fully arouse said snorer;

permitting said subject to initially terminate said unpleasant stimuli only while performing an assigned task requiring action in the fully awake state;

and finally terminating said unpleasant stimuli after the snorer has performed said task for a period long enough to ensure full wakefulness.

9. In combination, in a behavior modification device for training a snorer to cease snoring:
means for applying a selected one or more of plural aversive stimuli to the snorer to awaken him;

manually actuable means, accessible to the snorer when he awakens, for promptly deactivating the said means for applying a selected one or more of plural aversive stimuli;

time delay means, responsive to continued manual actuation of said manually actuatable means for a preselected period of time for initiating a controlled means at the end of said period of time;

said controlled means including means for providing pleasant positive reinforcement stimuli for said snorer.

10. The invention of claim 9 in which the means for applying a selected one or more of plural aversive stimuli to the snorer is manually controlled.

11. The invention of claim 9 in which the means for applying a selected one or more of plural aversive stimuli to the snorer is manually initiated into actuation.

12. The invention of claim 9 in which the means for applying a selected one or more of plural adversive stimuli to the snorer is automatically sequenced through a predetermined cycle.

* * * * *